(12) United States Patent
Jabbari

(10) Patent No.: US 12,343,445 B2
(45) Date of Patent: Jul. 1, 2025

(54) DRUG CONJUGATED NANOGELS IN MICROCAPSULE FOR DELAYED SUSTAINED PROTEIN DELIVERY

(71) Applicant: UNIVERSITY OF SOUTH CAROLINA, Columbia, SC (US)

(72) Inventor: Esmaiel Jabbari, Rockville, MD (US)

(73) Assignee: UNIVERSITY OF SOUTH CAROLINA, Columbia, SC (US)

( * ) Notice: Subject to any disclaimer, the term of this patent is extended or adjusted under 35 U.S.C. 154(b) by 1003 days.

(21) Appl. No.: 17/188,395

(22) Filed: Mar. 1, 2021

(65) Prior Publication Data

US 2021/0205493 A1   Jul. 8, 2021

Related U.S. Application Data

(62) Division of application No. 15/897,347, filed on Feb. 15, 2018, now Pat. No. 10,967,098.

(60) Provisional application No. 62/465,312, filed on Mar. 1, 2017.

(51) Int. Cl.
| A61L 27/26 | (2006.01) |
|---|---|
| A61L 27/36 | (2006.01) |
| A61L 27/38 | (2006.01) |
| A61L 27/54 | (2006.01) |
| A61L 27/58 | (2006.01) |

(52) U.S. Cl.
CPC .......... *A61L 27/26* (2013.01); *A61L 27/3612* (2013.01); *A61L 27/3633* (2013.01); *A61L 27/3834* (2013.01); *A61L 27/54* (2013.01); *A61L 27/58* (2013.01); *A61L 2300/414* (2013.01); *A61L 2300/622* (2013.01); *A61L 2300/64* (2013.01); *A61L 2400/06* (2013.01); *A61L 2400/12* (2013.01); *A61L 2430/06* (2013.01)

(58) Field of Classification Search
CPC ............... A61L 27/26; A61L 27/3612; A61L 27/3633; A61L 27/3834; A61L 27/54; A61L 27/58; A61L 2300/414; A61L 2300/622; A61L 2300/64; A61L 2400/06; A61L 2400/12; A61L 2430/06
See application file for complete search history.

(56) References Cited

U.S. PATENT DOCUMENTS

| 6,884,432 B2 | 4/2005 | Yaszemski et al. |
|---|---|---|
| 7,001,987 B2 | 2/2006 | Van Dyke |
| 7,642,300 B2 | 1/2010 | Yaszemski et al. |
| 9,101,654 B2 | 8/2015 | Jabbari |
| 9,314,549 B2 | 4/2016 | Jabbari |
| 9,808,555 B2 | 11/2017 | Jabbari |
| 10,723,774 B2 | 7/2020 | Jabbari |
| 10,836,994 B2 | 11/2020 | Jabbari |
| 10,967,098 B2 * | 4/2021 | Jabbari .............. A61L 27/3834 |
| 2007/0043202 A1 | 2/2007 | Yaszemski et al. |
| 2008/0206308 A1 | 8/2008 | Jabbari et al. |
| 2009/0324722 A1 | 12/2009 | Elisseeff |
| 2010/0084784 A1 | 4/2010 | Jabbari |
| 2010/0086607 A1 | 4/2010 | Jabbari |
| 2010/0322979 A1 | 12/2010 | Jabbari |
| 2010/0327494 A1 | 12/2010 | Jabbari |
| 2012/0226295 A1 | 9/2012 | Jabbari |
| 2014/0349367 A1 | 11/2014 | Jabbari |
| 2015/0175972 A1 | 6/2015 | Jabbari |
| 2018/0250438 A1 | 9/2018 | Jabbari |
| 2018/0251505 A1 | 9/2018 | Jabbari |
| 2018/0256780 A1 | 9/2018 | Jabbari |
| 2018/0273899 A1 | 9/2018 | Jabbari |
| 2020/0040296 A1 | 2/2020 | Jabbari |
| 2020/0360295 A1 | 11/2020 | Jabbari |

OTHER PUBLICATIONS

Lin C-C and Anseth KS "PEG Hydrogels for the Controlled Release of Biomaterials in REgenerative Medicine" Pharma. Res., Mar. 2009 (pub Dec. 18, 2008), 26(3), pp. 631-643; doi: 10.1007/s11095-008-9801-2. (Year: 2008).*

Jayasuriya CT, Chen Y, Liu W, Chen Q " The Influence of Tissue Microenvironment on Stem Cell-based Cartilage Repair" Ann NY Acad Sci (ANYAS), Nov. 2016; 1383(1): 21-33; doi: 10.1111/nyas. 13170. (Year: 2016).*

Andersen, et al. "Extremity War Injuries VIII: Sequelae of Combat Injuries" *J. Am. Acad. Ortho. Surg.* 22 (2014) pp. 57-62.

Anderson, et al. "Post-Traumatic Osteoarthritis: Improved Understanding and Opportunities for Early Intervention" *J. Orthop. Res.* 29 (2011) pp. 802-809.

Andrades, et al. "Induction of superficial zone protein (SZP)/lubricin/PRG 4 in muscle-derived mesenchymal stem/progenitor cells by transforming growth factor-beta1 and bone morphogenetic protein-7" *Arthr. Res. Ther.* 14:R72 (2012) pp. 1-7.

Annabi, et al. "Rational Design and Applications of Hydrogels in Regenerative Medicine" *Adv. Mater.* 26 (2014) pp. 85-124.

Aoyama, et al. "Keratin Nanofiber Scaffold for Vascular Graft" *Tiss. Eng. A* 21 (2015) p. S244.

Arai et al. "Amino-acid sequence of feather keratin from fowl" *Eur. J. Biochem.* 132 (1983) pp. 506-507.

Audouin, et al. "Surface-initiated RAFT polymerization of NIPAM from monolithic macroporous poly HIPE" *Euro. Polym. J.* 49 (2019) pp. 1073-1079.

Balaji, et al. "Characterization of keratin collagen 3D scaffold for biomedical applications" *Polym. Adv. Tech.* 23 (2012) pp. 500-507.

(Continued)

*Primary Examiner* — Aaron J Kosar
(74) *Attorney, Agent, or Firm* — DORITY & MANNING, P.A.

(57) ABSTRACT

Injectable compositions and use of the injectable compositions in tissue engineering applications are described. The injectable compositions are hydrogel-based compositions that can be crosslinked in situ following placement. The injectable compositions include microcapsules having predetermined erosion profiles that are loaded with nanogels having predetermined sustained release profiles for signaling molecules conjugated to the nanogels. Following crosslinking, the compositions are designed to sequentially release signaling molecules over a predetermined period of time with various release profiles. The compositions can carry additional components to stimulate tissue generation such as stem cells and extracellular matrix (ECM) components.

20 Claims, 8 Drawing Sheets

(56) References Cited

OTHER PUBLICATIONS

Barati, et al. "Effect of Organic Acids on Calcium Phosphate Nucleation and Osteogenic Differentiation of Human Mesenchymal Stem Cells on Peptide Functionalized Nanofibers" *Langmuir* 31 (2015) pp. 5130-5140.

Barati, et al. "Spatiotemporal release of BMP-2 and VEGF enhances osteogenic and vasculogenic differentiation of human mesenchymal stem cells and endothelial colony-forming cells coencapsulated in a patterned hydrogel" *J. Contr. Rel.* 223 (2016) pp. 126-136.

Barati, et al. "Synthesis and characterization of photocrosslinkable keratin hydrogels for stem cell Encapsulation" Biomacromolecules 18 (2017) pp. 398-412.

Barati, et al. "Time dependence of material properties of polyethylene glycol hydrogels chain extended with short hydroxy acid segments" *Polymer* 55 (2014) pp. 3894-3904.

Barone, et al. "Thermally processed keratin films" *J. Appl. Polym. Sci.* 97 (2005) pp. 1644-1651.

Beck, et al. "Approaching the compressive modulus of articular cartilage with a decellularized cartilage-based hydrogel" *Acta Biomaterialia* 38 (2016) pp. 94-105.

Bernardes, et al. "Facile conversion of cysteine and alkyl cysteines to dehydroalanine on protein surfaces: versatile and switchable access to functionalized proteins" *J. Am. Chem. Soc.* 130 (2008) pp. 5052-5053.

Bhardwaj, et al. "Silk fibroin-keratin based 3D scaffolds as a dermal substitute for skin tissue engineering" *Integr. Biol.* 7 (2015) pp. 53-63.

Burnett, et al. "Hemostatic properties and the role of cell receptor recognition in human hair keratin protein hydrogels" *Biomaterials* 34 (2013) pp. 2632-2640.

Chalker, et al. "Chemical modification of proteins at cysteine: opportunities in chemistry and biology" *Chemistry* 4 (2009) pp. 630-640.

Chan, et al. "Crosslinking of collagen scaffolds promotes blood and lymphatic vascular stability" *J. Biomed. Mater. Res.* A 102 (2014) pp. 3186-3195.

Chen, et al. "A Universal and Facile Approach for the Formation of a Protein Hydrogel for 3D Cell Encapsulation" *Adv. Funct. Mater.* 25 (2015) pp. 6189-6198.

Chen, et al. "Engineering Vascularized Tissue Constructs using an Injectable Cell-laden Collagen Hydrogel" *Tiss. Eng.* A 21 (2015) p. S-102.

Dawson, et al. "Biomaterials for stem cell differentiation" *Adv. Drug Del. Rev.* 60 (2008) pp. 215-228.

D'Este, et al. "Evaluation of an injectable thermoresponsive hyaluronan hydrogel in a rabbit osteochondral defect model" J. Biomed. Mater. Res. A 104 (2016) pp. 1469-1478.

Dong, et al. "In Situ 'Clickable' Zwitterionic Starch-Based Hydrogel for 3D Cell Encapsulation" ACS *Appl. Mater. Interf.* 8 (2016) pp. 4442-4455.

Dong, et al. "Injectable Hybrid Hydrogel for Mesenchymal Stem Cell Delivery, from PEG-based Multifunctional Hyperbranched Polymers" *Tiss. Eng.* A 21 (2015) pp. S298-S299.

Eastoe, J.E. "The amino acid composition of mammalian collagen and gelatin" *Biochem. J.* 61 (1955) pp. 589-600.

Evans, et al. "Use of Genetically Modified Muscle and Fat Grafts to Repair Defects in Bone and Cartilage" Eur. Cells Mater. 18 (2009) pp. 96-111.

Falah, et al. "Treatment of articular cartilage lesions of the knee." *Int'l Ortho.* 34 (2010) pp. 621-630.

Ferlin, et al. "Development of a Dynamic Stem Cell Culture Platform for Mesenchymal Stem Cell Adhesion and Evaluation" *Molec. Pharma.* 11 (2014) pp. 2172-2181.

Fuhrmann, et al. "Injectable hydrogel promotes early survival of induced pluripotent stem cell-derived oligodendrocytes and attenuates longterm teratoma formation in a spinal cord injury model" *Biomaterials* 83 (2016) pp. 23-36.

Fukumoto, et al. "Combined effects of insulin-like growth factor-1 and transforming growth factor-ß 1 on periosteal mesenchymal cells during chondrogenesis in vitro" *Osteoarthr. Cart.* 11 (2003) pp. 55-64.

Golub, et al. "The Role of Alkaline Phosphatase in Cartilage Mineralization" *Bone Miner.* 17 (1992) pp. 273-278.

Gorman, J. "Materials Take Wing: What to do with 4 billion pounds of feathers?" *Sci. News* 161 (2002) pp. 120-121.

Grogan, et al. "Zone-Specific Gene Expression Patterns in Articular Cartilage" *Arthr. Rheum.* 65 (2013) pp. 418-428.

Guo, et al. "In vitro generation of an osteochondral construct using injectable hydrogel composites encapsulating rabbit marrow mesenchymal stem cells" *Biomaterials* 30 (2009) pp. 2741-2752.

Han, et al. "Alkylation of human hair keratin for tunable hydrogel erosion and drug delivery in tissue engineering applications" *Acta Biomaterialia* 23 (2015) pp. 201-213.

Han, et al. "Bioerodable PLGA-Based Microparticles for Producing Sustained-Release Drug Formulations and Strategies for Improving Drug Loading" *Front. Pharmacol.* 7 (2016) pp. 1-11.

He, et al. "Effect of grafting RGD and BMP-2 protein-derived peptides to a hydrogel substrate on osteogenic differentiation of marrow stromal cells" *Langmuir* 24 (2008) pp. 12508-12516.

Hoffman, A.S. "Hydrogels for biomedical applications" *Adv. Drug Del. Rev.* 64 (2012) pp. 18-23.

Holland, et al. "Dual growth factor delivery from degradable oligo(poly(ethylene glycol) fumarate) hydrogel scaffolds for cartilage tissue engineering" *J. Contr. Rel.* 101 (2005) pp. 111-125.

Jayasuriya, et al. "The influence of tissue microenvironment on stem cell-based cartilage repair" *Ann. NY Acad. Sci.* 1383 (2016) pp. 21-33.

Jayathilakan, et al. "Utilization of byproducts and waste materials from meat, poultry and fish processing industries: a review" *J. Food Sci. Tech.* 49 (2012) pp. 278-293.

Kakkar, et al. "Extraction and characterization of keratin from bovine hoof: A potential material for biomedical applications" *SpringerPlus* 3:596 (2014) pp. 1-9.

Karaman, et al. "Effect of surface modification of nanofibres with glutamic acid peptide on calcium phosphate nucleation and osteogenic differentiation of marrow stromal cells" *J. Tiss. Eng. Regener. Med.* 10 (2016) pp. E132-E146.

Karimi, et al. "A developmentally inspired combined mechanical and biochemical signaling approach on zonal lineage commitment of mesenchymal stem cells in articular cartilage regeneration" *Integr. Biol.* 7 (2015) pp. 112-127.

Kelly, et al. "How to study proteins by circular dichroism" *Biochimica et Biophysica Acta* 1751 (2005) pp. 119-139.

Klein, et al. "Depth-dependent biomechanical and biochemical properties of fetal, newborn, and tissue-engineered articular cartilage" *J. Biomech.* 40 (2007) pp. 182-190.

Kwon, et al. "In vivo osteogenic differentiation of human turbinate mesenchymal stem cells in an injectable in situ-forming hydrogel" *Biomaterials* 35 (2014) pp. 5337-5346.

Lam, et al. "Osteochondral defect repair using bilayered hydrogels encapsulating both chondrogenically and osteogenically pre-differentiated mesenchymal stem cells in a rabbit model" *Osteoarthr. Cartil.* 22 (2014) pp. 1291-1300.

Lee, et al. "Production of nanoparticles-in-microparticles by a double emulsion method: A comprehensive study" *Eur. J. Pharm. Biopharm.* 83 (2013) pp. 168-173.

Lee, et al. "Regeneration of the articular surface of the rabbit synovial joint by cell homing: a proof of concept study" *Lancet* 376 (2010) pp. 440-448.

Li, et al. "The Effect of Oxygen Tension on Human Articular Chondrocyte Matrix Synthesis: Integration of Experimental and Computational Approaches" *Biotech. Bioeng.* 111 (2014) pp. 1876-1885.

Lin, et al. "Allyl sulfides are privileged substrates in aqueous cross-metathesis: application to site- selective protein modification" *J. Am. Chem. Soc.* 130 (2008) pp. 9642-9643.

Lin, et al. "PEG hydrogels for the controlled release of biomolecules in regenerative medicine" *Pharma. Res.* 26 (2009) pp. 631-643.

(56) References Cited

OTHER PUBLICATIONS

Long, et al. "Improving the mechanical properties of collagen-based membranes using silk fibroin for corneal tissue engineering" *J. Biomed. Mater. Res. A* 103 (2015) pp. 1159-1168.

Lotz, M.K. "Posttraumatic osteoarthritis: pathogenesis and pharmacological treatment options" *Arthr. Res. Ther.* 12:211 (2010) pp. 1-9.

Lv, et al. "Structural and functional evaluation of oxygenating keratin/silk fibroin scaffold and initial assessment of their potential for urethral tissue engineering" *Biomaterials* 84 (2016) pp. 99-110.

Ma, et al. "Enhanced biological stability of collagen porous scaffolds by using amino acids as novel cross-linking bridges" *Biomaterials* 25 (2004) pp. 2997-3004.

Mabry, et al. "Microarray analyses to quantify advantages of 2D and 3D hydrogel culture systems in maintaining the native valvular interstitial cell phenotype" *Biomaterials* 74 (2016) pp. 31-41.

Mak, et al. "Indian hedgehog signals independently of PTHrP to promote chondrocyte hypertrophy" *Development* 135 (2008) pp. 1947-1956.

Makadia, et al. "Poly Lactic-co-Glycolic Acid (PLGA) as Biodegradable Controlled Drug Delivery Carrier" *Polymers* 3 (2011) pp. 1377-1397.

Mariani, et al. "Signaling Pathways in Cartilage Repair" *Int'l J. Molecul. Sci.* 15 (2014) pp. 8667-8698.

Melrose, et al. "Chondroitin sulphate and heparan sulphate sulphation motifs and their proteoglycans are involved in articular cartilage formation during human foetal knee joint development" *Histochem. Cell Biol.* 138 (2012) pp. 461-475.

Mercado, et al. "Effect of grafting BMP2-derived peptide to nanoparticles on osteogenic and vasculogenic expression of stromal cells" *J. Tiss. Eng. Regen. Med.* 8 (2014) pp. 15-28.

Mi, et al. "Adverse effects of adenovirus-mediated gene transfer of human transforming growth factor beta 1 into rabbit knees" *Arthr. Res. Ther.* 5 (2003) pp. R132-R139.

Moeinzadeh, et al. "Comparative effect of physicomechanical and biomolecular cues on zone- specific chondrogenic differentiation of mesenchymal stem cells" *Biomaterials* 92 (2016) pp. 57-70.

Moeinzadeh, et al. "Gelation Characteristics and Osteogenic Differentiation of Stromal Cells in Inert Hydrolytically Degradable Micellar Polyethylene Glycol Hydrogels" *Biomacromolecules* 13 (2012) pp. 2073-2086.

Moeinzadeh, et al. "Nanostructure Formation and Transition from Surface to Bulk Degradation in Polyethylene Glycol Gels Chain-Extended with Short Hydroxy Acid Segments" *Biomacromolecules* 14 (2013) pp. 2917-2928.

Munoz-Pinto, et al. "Collagen-mimetic hydrogels promote human endothelial cell adhesion, migration and phenotypic maturation" *J. Mater. Chem. B* 3 (2015) pp. 7912-7919.

Namba, et al. "Spontaneous repair of superficial defects in articular cartilage in a fetal lamb model" *J. Bone Joint Surg. Am.* 80A (1998) pp. 4-10.

Nguyen, et al. "Engineering articular cartilage with spatially-varying matrix composition and mechanical properties from a single stem cell population using a multi-layered hydrogel" *Biomaterials* 32 (2011) pp. 6946-6952.

Nichol, et al. "Cell-laden microengineered gelatin methacrylate hydrogels" *Biomaterials* 31 (2010) pp. 5536-5544.

Oliver-Welsh, et al. "Deciding how best to treat cartilage defects" *Orthopedics* 39 (2016) pp. 343-350.

Orth et al. "Reliability, Reproducibility, and Validation of Five Major Histological Scoring Systems for Experimental Articular Cartilage Repair in the Rabbit Model" *Tiss. Eng. C Meth.* 18 (2012) pp. 329-339.

Pace, et al. "A Human Hair Keratin Hydrogel Scaffold Enhances Median Nerve Regeneration in Nonhuman Primates: An Electrophysiological and Histological Study" *Tiss. Eng. A* 20 (2014) pp. 507-517.

Pascher, et al. "Gene delivery to cartilage defects using coagulated bone marrow aspirate" *Gene Ther.* 11 (2004) pp. 133-141.

Patel, et al. "Biodegradable polymer scaffold for tissue engineering" *Trends Biomater. Artif. Org.* 25 (2011) pp. 20-29.

Pfaff, K "A third of soldiers disabled after ACI for lesions in the knee" *Ortho. Today* (2014) pp. 1-2.

Punzi, et al. "Post-traumatic arthritis: overview on pathogenic mechanisms and role of inflammation" *Rheum. Musculoskel. Dis.* 2:e000279 (2016) pp. 1-9.

Rehmann, et al. "Tuning microenvironment modulus and biochemical composition promotes human mesenchymal stem cell tenogenic differentiation" *J. Biomed. Mater. Res. A* 104 (2016) pp. 1162-1174.

Rivera, et al. "Post-traumatic OA: Unique implications for the military" *Lower Extrem. Rev.* (2013) pp. 43-46.

Rivera, et al. "Posttraumatic osteoarthritis caused by battlefield injuries: the primary source of disability in warriors" *J. Am. Acad. Orthop. Surg.* 20 (2012) pp. S64-S69.

Rouse, et al. "A Review of Keratin-Based Biomaterials for Biomedical Applications" *Materials* 3 (2010) pp. 999-1014.

Saravanan, et al. "Exploration on the Amino Acid Content and Morphological Structure in Chicken Feather Fiber" *J. Text. Appar. Tech. Mgmt.* 7 (2012) pp. 1-6.

Sawada, et al. "Scaffold for Cell Culture Made by Electrospun Keratin Nanofibers" *Tiss. Eng. A* 20 (2014) p. S-65.

Simank, et al. "Effects of local application of growth and differentiation factor-5 (GDF-5) in a full-thickness cartilage defect model" *Growth Factors* 22 (2004) pp. 35-43.

Srinivasan, et al. "Injectable perlecan domain 1-hyaluronan microgels potentiate the cartilage repair effect of BMP2 in a murine model of early osteoarthritis" *Biomed. Mater.* 7:024109 (2012) pp. 1-11.

Stenman, et al. "Trypsin-2 degrades human type II collagen and is expressed and activated in mesenchymally transformed rheumatoid arthritis synovitis tissue" *Am. J. Path.* 167 (2005) pp. 1119-1124.

Stockwell, R.A. "Interrelationship of Cell Density and Cartilage Thickness in Mammalian Articular Cartilage" *J. Anat.* 109 (1971) pp. 411-421.

Studer, et al. "Molecular and Biophysical Mechanisms Regulating Hypertrophic Differentiation in Chondrocytes and Mesenchymal Stem Cells" *Eur. Cells Mater.* 24 (2012) pp. 118-135.

Tan, et al. "Fabrication and Evaluation of Porous Keratin/chitosan (KCS) Scaffolds for Effectively Accelerating Wound Healing" *Biomed. Envir. Sci.* 28 (2015) pp. 178-189.

Tanabe, et al. "Fabrication and characterization of chemically crosslinked keratin films" *Mater. Sci. Eng. C* 24 (2004) pp. 441-446.

Tropel, et al. "Isolation and characterization of mesenchymal stem cells from adult mouse bone marrow" *Exp. Cell Res.* 295 (2004) pp. 395-406.

Verma, et al. "Preparation of scaffolds from human hair proteins for tissue-engineering applications" *Biomed. Mater. C* 3:025007 (2008) pp. 1-12.

Verschure, et al. "Localization of insulin-like growth factor-1 receptor in human normal and osteoarthritic cartilage in relation to proteoglycan synthesis and content" Br. *J. Rheumatol.* 35 (1996) pp. 1044-1055.

Visser, et al. "Crosslinkable Hydrogels Derived from Cartilage, Meniscus, and Tendon Tissue" *Tiss. Eng. A* 21 (2015) pp. 1195-1206.

Wagegg, et al. "Hypoxia Promotes Osteogenesis but Suppresses Adipogenesis of Human Mesenchymal Stromal Cells in a Hypoxia-Inducible Factor-1 Dependent Manner" *PloS One* 7:e46483 (2012) pp. 1-11.

Wang, et al. "Culturing fibroblasts in 3D human hair keratin hydrogels" *Appl. Mater. Interf.* 7 (2015) pp. 5187-5198.

Wang, et al. "Human keratin hydrogels support fibroblast attachment and proliferation in vitro" *Cell Tiss. Res.* 347 (2012) pp. 795-802.

Wang, et al. "TGFβ signaling in cartilage development and maintenance" *Birth Def. Res. C Embryo Today Rev.* 102 (2014) pp. 37-51.

Watson, et al. "Gene delivery of TGF-β1 induces arthrofibrosis and chondrometaplasia of synovium in vivo" *Lab. Invest.* 90 (2010) pp. 1615-1627.

(56) References Cited

OTHER PUBLICATIONS

Wehling, et al. "Interleukin-1 β and Tumor Necrosis Factor α Inhibit Chondrogenesis by 16 Human Mesenchymal Stem Cells Through NF-KB-Dependent Pathways" Arthr. Rheum. 60 (2009) pp. 801-812.
Williamson, et al. "Growth of immature articular cartilage in vitro: Correlated variation in tensile biomechanical and collagen network properties" *Tiss. Eng.* 9 (2003) pp. 625-634.
Wong, et al. "Chondrocyte biosynthesis correlates with local tissue strain in statically compressed adult articular cartilage" *J. Ortho. Res.* 15 (1997) pp. 189-196.
Wu, et al. "Human developmental chondrogenesis as a basis for engineering chondrocytes from pluripotent stem cells" *Stem Cell Rep.* 1 (2013) pp. 575-589.
Xu, et al. "Water-Stable Three-Dimensional Ultrafine Fibrous Scaffolds from Keratin for Cartilage Tissue Engineering" *Langmuir* 30 (2014) pp. 8461-8470.
Yamauchi, et al. "Preparation of stable aqueous solution of keratins, and physiochemical and biodegradational properties of films" *J. Biomed. Mater. Res.* 31 (1996) pp. 439-444.
Yang, et al. "Engineering Orthopedic Tissue Interfaces" *Tiss. Eng. B Rev.* 15 (2009) pp. 127-141.
Yin, et al. "Study on effective extraction of chicken feather keratins and their films for controlling drug release" *Biomater. Sci.* 1 (2013) pp. 528-536.
Yue, et al. "Synthesis, properties, and biomedical applications of gelatin methacryloyl (GelMA) hydrogels" *Biomaterials* 73 (2015) pp. 254-271.
Zhang, et al. "The role of tissue engineering in articular cartilage repair and regeneration" *Crit. Rev. Biomed. Eng.* 37 (2009) pp. 1-57.

\* cited by examiner

DRUG CONJUGATED NANOGELS IN MICROCAPSULE FOR DELAYED SUSTAINED PROTEIN DELIVERY

CROSS REFERENCE TO RELATED APPLICATION

This application is a divisional application of U.S. patent application Ser. No. 15/897,347, having a filing date of Feb. 15, 2018, which claims filing benefit of U.S. Provisional Patent Application Ser. No. 62/465,312, having a filing date of Mar. 1, 2017, which are incorporated herein by reference for all purposes.

BACKGROUND

Natural tissue formation and differentiation takes place according to a well-ordered process that is controlled by sequential expression of signaling molecules. For instance, during embryonic development of cartilage, mesenchymal stem cells (MSCs) condense by up-regulation of transforming growth factor-β1 (TGFβ1) signaling. The condensed MSCs differentiate into pre-chondrocytes by co-expression of TGFβ1 and bone morphogenetic protein-7 (BMP7) to form a matrix remarkably similar to the superficial zone of articular cartilage. Next, the developing fetal cartilage divides into two morphologically distinct zones, namely the superficial and middle zones, by further differentiation of pre-chondrocytes to pre-hypertrophic chondrocytes driven by the gradients in BMP7 and insulin-like growth factor-1 (IGF1). In a similar process, the cells further away from the synovial cavity mature into hypertrophic chondrocytes by gradients in BMP7, IGF1, and Indian Hedgehog (IHH) to generate the complete zonal organization (superficial, middle, calcified) of articular cartilage. Early morphogenetic events are also significantly affected by the local environment of the developing tissue. For instance, during the embryonic development of cartilage, in addition to the sequential expression of morphogens, the extracellular matrix (ECM) motifs in fetal articular cartilage play a significant development role.

Unfortunately, later in the life cycle, the body is no longer able to generate tissue in repair/replacement processes as effectively as is possible during embryonic development. For instance, fetal articular cartilage injuries are able to heal spontaneously and avoid fibrous scar tissue, while postnatal articular cartilage lacks the ability for complete self-repair.

The inability of tissue damage to heal effectively can lead to issues due to scar tissue formation, as well as long term tissue damage. A significant consequence of traumatic extremity injuries and the inability for self-repair of articular cartilage is post-traumatic osteoarthritis (PTOA). The rapidly applied load in traumatic injuries focally disrupts the articular cartilage beginning with cell death, decreased stiffness, and rapid progression to a full-thickness defect with time. Approximately 12% of all osteoarthritis (OA) cases are caused by PTOA. About 3.5 million individuals in the US suffer from PTOA of the hip, knee, or ankle with a total cost of $3 billion to the health care system. PTOA can occur in any age from any acute physical trauma such as sport, vehicle accident, fall, or military injury.

Unfortunately, treatment of tissue damage absent of, or only minimally supported by, the benefit of natural repair mechanisms remains limited in effectiveness. Conventional clinical approaches to treatment of full-thickness chondral defects such as subchondral drilling, microfracture, and abrasion arthroplasty create mechanically inferior fibrocartilage. Osteochondral autograft transfer or mosaicplasty suffers from an additional surgical intervention and donor site morbidity. Autologous chondrocyte implantation (ACI) fails to restore zonal organization of the articular cartilage and, in some cases, leads to peripheral hypertrophy and calcification. For example, 33% of ACI procedures performed on soldiers suffering from PTOA of the knee resulted in permanent disability. Tissue engineered (TE) articular cartilage grafts have also been developed. As the middle zone is the thickest layer and bears the bulk of the compressive load, most TE articular cartilage grafts are based on mimicking the properties of the middle zone. However, these grafts have been shown to degenerate into biologically inferior fibrocartilage tissue.

What are needed in the art are improved compositions for use in reconstruction and repair of damaged tissue that can more closely mimic and encourage the body's natural tissue formation mechanisms. For instance, injectable therapies that can regenerate the zonal microstructure of articular cartilage would be of great benefit in the art and have the potential to prevent permanent disability in patients suffering from PTOA.

SUMMARY

A composition is disclosed for use in tissue engineering applications. The composition includes nano-sized particles (i.e., nanogels) that include a crosslinked polymer conjugated to a signaling molecule (e.g., a protein or a functional fragment of a protein) that encourages some aspect of tissue formation/repair. For example, a signaling molecule can include an expression product that has efficacy in stem cell differentiation and/or tissue formation (e.g., TGFβ1, BMP7, IGF1, IHH, BMP2, vascular endothelial growth factor (VEGF), etc.). The crosslinked polymer of the nanogel is designed to degrade over a predetermined time period and thus provide for sustained release of the signaling molecule over a desired period of time.

The composition can also include a plurality of microcapsules, and each microcapsule can carry a plurality of the nanogels. Each nanogel of a single microcapsule can carry the same signaling molecule (or combination of signaling molecules) as one another. Alternatively, the nanogels held within a single microcapsule can vary from one another. The microcapsules can include a bioerodible polymer that is designed to exhibit a controlled release profile for the nanogels carried inside. As such, the release of the nanogels (and the subsequent sustained release of the signaling molecule(s) carried by the nanogels) can be controlled (e.g., delayed) following placement of the composition at a targeted location, e.g., via injection. For instance, a composition can carry a first set of microcapsules that release the nanogels immediately following placement of the composition. The composition can also carry a second set of microcapsules that release the nanogels only after a predesigned delay period. Thus, the signaling molecules of the nanogels can be released into the area according to a sequential and sustained release profile.

The composition can also include a crosslinkable polymer and can define a rheology suitable for injection to a targeted site. Following placement of the composition, the polymer can be crosslinked in situ by application of energy (e.g., UV crosslinking, temperature-based crosslinking, etc.) so as to form a semi-solid, crosslinked hydrogel at a location of desired tissue formation.

The crosslinkable composition can include a plurality of the microcapsules (that, in turn, each carry a plurality of nanogels), as well as additional components for tissue engineering. For instance, a composition can carry differentiated or stem cells (e.g., mesenchymal stem cells) that can be affected by the sequential release of the signaling molecules from the nanogels to form the desired tissue. The composition can also carry extracellular matrix motifs for the particular environment of the desired tissue formation. For instance, in the formation of articular cartilage, a composition can include a fetal articular cartilage extracellular matrix mimetic.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Figure 1:
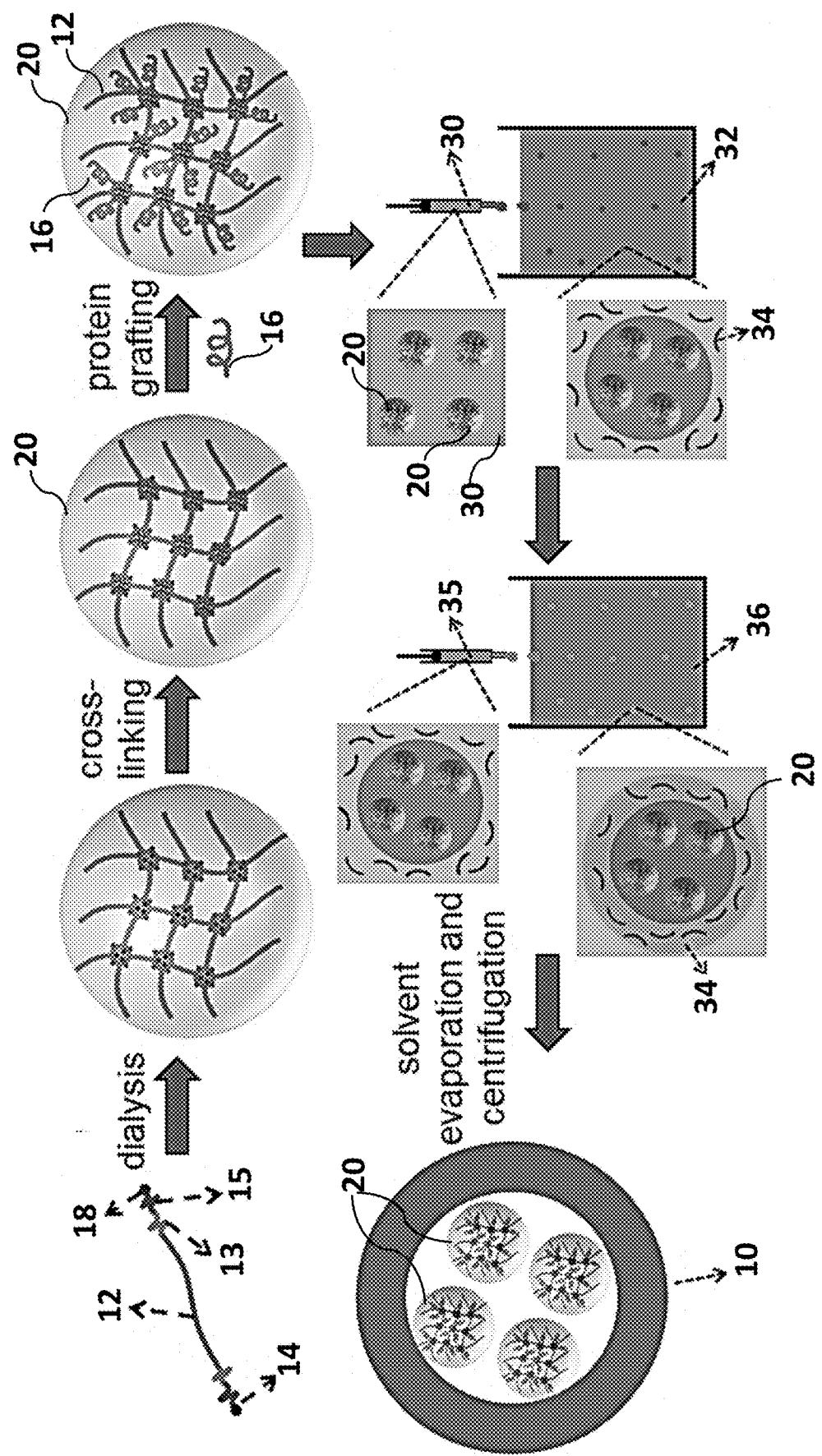
FIG. 1 schematically illustrates a synthesis process as may be utilized in formation of a composition as described herein.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, disclosed herein are compositions and use of the compositions in tissue engineering applications. The compositions are hydrogel-based compositions that can be crosslinked in situ following placement and are designed to sequentially release multiple (i.e., at least two) signaling molecules over a predetermined period of time so as to encourage tissue development or healing in the local area. The compositions can also carry additional components to encourage tissue generation. For instance, a composition can carry cells (either differentiated cells or stem cells) that can interact with the signaling molecules in the tissue generation. In addition, a composition can carry extracellular matrix (ECM) components that can further encourage tissue generation. In one particular embodiment, a composition can have characteristics so as to be injectable prior to crosslinking.

While much of the following discussion is directed to development of articular cartilage, the disclosure is in no way intended to be limited to compositions and methods for articular cartilage engineering applications, and through selection of particular signaling molecules, release profiles, ECM components, cell types, etc., the compositions can be utilized in development of other types of tissues including, without limitation, bone, connective tissues, etc.

The compositions described herein allow for not only the sustained release of signaling molecules (e.g., proteins), but also allow for the delayed release of signaling molecules, to stimulate tissue healing/generation in order that the sequential signaling naturally present in tissue formation/healing can be mimicked in the tissue engineering applications. In the absence of sequential and sustained delivery, signaling molecules that are merely located at a desired site of activity will diffuse away from the site of regeneration within a few hours and gradients necessary for desired biological activity will disappear. By way of example, in order to mimic fetal development of articular cartilage, morphogens (e.g., BMP2, IGF1, IHH) need to be available both sequentially and sustainably.

In formation of the compositions, signaling molecules such as known primary articular cartilage morphogens can be conjugated to nanogels so as to provide for sustained release of the morphogens from the nanogels. In addition, the nanogels that carry the signaling molecules can be encapsulated in microcapsules that can provide for delayed release of the nanogels. Through combination of the nanogels and the microcapsules, optionally in conjunction with additional tissue engineering components (e.g., ECM components, stem cells, etc.), the compositions can be utilized for tissue engineering that more closely mimics natural tissue generation mechanisms.

FIG. 1 schematically illustrates one embodiment for formation of the composite microcapsule/nanogel structures of a composition. As shown, a composite structure can include a microcapsule 10 that encapsulate a plurality of nanogels 20. Each nanogel 20 includes a polymer 12 that in turn includes a first functionality 14 configured for conjugation with a signaling molecule 16 and a second functionality 18 configured for crosslinking of the polymer. The combination of microcapsules 10 that can be designed to delayed release of the contents with the sustained releasing nanogels 20 held within the microcapsules 10 can provide for delayed/sustained release of the signaling molecules. When considering an articular cartilage tissue engineering composition, a composition that includes a plurality of composite nanogel/microcapsule types that differ by release profile and signaling molecule can provide for delayed/sustained release of the signaling molecules (e.g., TGFβ1, BMP7, IGF1, and IHH) for sequential differentiation of stem cells that can also be carried by the composition to pre-chondrogenic, pre-hypertrophic, and hypertrophic cell phenotypes of articular cartilage in a sequential fashion that can mimic natural tissue development.

Referring to FIG. 1, the nanogels 20 can be formed of a biocompatible polymer 12 that can be derivatized as necessary so as to be crosslinkable via the presence of a functionality 18, controllably degradable in a biological environment (e.g., hydrolysable), and capable of conjugation to the signaling molecules 16 via the presence of a reactive functionality 14.

While any hydrophilic polymer can be used as a base for the synthesis of nanogels, in one embodiment, the nanogels can be based upon a polyethylene glycol (PEG) polymer. Other hydrophilic polymers that can be used include, without limitation, polyvinyl alcohol, polyvinyl pyrrolidinone, polyacrylic acid, poly(2-hydroxyethyl methacrylate), poly(acrylamide), and the like, as well as mixtures of the aforementioned hydrophilic polymers. PEG-based hydrogels are inert, non-immunogenic, compatible with biological components (e.g., stem cells) and can be derivatized relatively easily. Due to their inert nature, PEG hydrogels provide enormous flexibility in design and control of the local microenvironment. The inert nature of PEG can also minimize adsorption and denaturation of signaling molecules (e.g., proteins) incorporated in the nanogels, which could otherwise adversely affect the composition function, and can stabilize the signaling molecules by reducing aggregation. Beneficially, flexible PEG polymers can crosslink to produce hydrogels with high compressive modulus without adversely affecting the function of the conjugated signaling molecules. The PEG polymers can impart stability to the nanogels in aqueous solution.

In general, the polymer 12 used in formation of the nanogels 20 can have a number average molecular weight of from about 4 kDa to about 12 kDa.

In order to control self-assembly of the polymer 12 in the initial formation of the nanogels and degradation of the nanogels according to a desired sustained release profile for the conjugated signaling molecules, the polymer 12 can be chain extended at the termini with relatively short hydrophobic segments that include a series of hydrophobic monomers. The hydrophobic monomers can include any biocompatible hydrophobic monomers such as, without limitation, lipid monomers, anhydride monomers, orthoester monomers, phosphazene monomers, hydroxy acid monomers, and the like, as well as mixtures of hydrophobic monomers. For instance, the hydrophobic segment can include, without limitation, glycolide monomers, lactide monomers, dioxanone monomers, ε-caprolactone monomers, hydroxy butyrate monomers, valerolactone monomers, malonic acid monomers, as well as mixtures of monomers.

In one embodiment, a hydrophobic segment of a polymer 12 terminus can include a first length 13 that includes a series of lactide monomers that can regulate self-assembly of the nanogels and a second length 15 that includes a series of glycolide monomers that can aid in control of the degradation rate of the nanogel. Each length 13, 15 of a hydrophobic segment can be about 10 monomer units in length or less. For instance, the length 13 of lactide monomers can generally include from 2 to about 9 monomer units and the length 15 of glycolide monomers can generally include from 1 to about 6 monomer units.

The short hydrophobic segments 13, 15 can be bonded to the polymer 12 according to any suitable process, such as by combining the polymer with the hydrophobic monomer under reactive conditions with a catalyst, e.g., a tin(II)2-ethylhexanoate catalyst.

Without wishing to be bound to any particular theory, it is believed that the short hydrophobic segments can be sequestered within the core of the nanogels formed during the crosslinking reactions. In addition, the crosslinking moieties and any initiators used in conjunction with the crosslinking reaction can be sequestered within the nanogel core. By sequestering self-assembly, gelation and degradation components within the crosslinked nanogel structures, potential cytotoxicity of the nanogels to cells or other components of the composition can be reduced.

Furthermore, the size of each individual nanogel can be controlled by specific components used to form the nanogel particles (e.g., the polymer size and relative hydrophobicity of the short terminal segments), and the nanogel size can affect the degradation rate of the nanogels. The degradation rate of the nanogels and sustained release of the signaling molecules carried in the nanogels can be tuned from a few days to many months through variation of the polymer size, as well as the characteristics of the hydrophobic end segments. The hydrolysis rate of the nanogels can be strongly dependent on the number and type of hydrophobic monomers in the hydrophobic segment. For instance, a nanogel that incorporates a less hydrophobic monomer, such as glycolide, can release the signaling molecules over the course of a few days, while one that incorporates a more hydrophobic monomer, such as ε-caprolactone, can release the signaling molecules over the course of many months.

The polymers 12 can also be functionalized with a reactive functionality 18 that can provide for crosslinking of the polymers 12 and formation of stable nanogels 20. Accordingly, in addition to the chain extension of the polymers with the hydrophobic segments, a polymer 12 can be further processed to promote crosslinking of the polymer and formation of the crosslinked nanogels. For example, to crosslink the polymers 12 via UV, the polymer 12 can be functionalized at the termini to have a UV-crosslinkable functionality 18. Such groups are typically acrylates or methacrylates. The general scheme can include replacing terminal hydroxyl and/or carboxylic acid groups of a hydrophobic segment with acrylate or methacrylate functionality according to standard practice.

Crosslinking may be carried out via self-crosslinking of the polymer and/or through the inclusion of a separate crosslinking agents and/or initiators. Suitable crosslinking agents, for instance, may include polyglycidyl ethers, such as ethylene glycol diglycidyl ether and polyethylene glycol diglycidyl ether; acrylamides; compounds containing one or more hydrolyzable groups, such as alkoxy groups (e.g., methoxy, ethoxy and propoxy); alkoxyalkoxy groups (e.g., methoxyethoxy, ethoxyethoxy and methoxypropoxy); acyloxy groups (e.g., acetoxy and octanoyloxy); ketoxime groups (e.g., dimethylketoxime, methylketoxime and methylethylketoxime); alkenyloxy groups (e.g., vinyloxy, isopropenyloxy, and 1-ethyl-2-methylvinyloxy); amino groups (e.g., dimethylamino, diethylamino and butylamino); aminoxy groups (e.g., dimethylaminoxy and diethylaminoxy); and amide groups (e.g., N-methylacetamide and N-ethylacetamide).

If included, an initiator can be used to initiate crosslinking of the polymer 12. Examples of UV initiators include, without limitation, IRGACURE® 184 (1-hydroxycyclohexyl phenyl ketone) and DAROCURE® 1173 (α-hydroxy-1, α-dimethylacetophenone) which are both commercially available from Ciba-Geigy Corp. Additional examples of initiators (which may be UV-initiators, thermal initiators, or other types of initiators) may include, without limitation, benzoyl peroxide, azo-bis-isobutyronitrile, di-t-butyl peroxide, bromyl peroxide, cumyl peroxide, lauroyl peroxide, isopropyl percarbonate, methylethyl ketone peroxide, cyclohexane peroxide, t-butylhydroperoxide, di-t-amyl peroxide, dicumyl peroxide, t-butyl perbenzoate, benzoin alkyl ethers (such as benzoin, benzoin isopropyl ether, and benzoin isobutyl ether), benzophenones (such as benzophenone and methyl-o-benzoyl benzoate), acetophenones (such as acetophenone, trichloroacetophenone, 2,2-diethoxyacetophenone, p-t-butyltrichloro-acetophenone, 2,2-dimethoxy-2-phenylacetophenone, and p-dimethylaminoacetophenone), thioxanthones (such as xanthone, thioxanthone, 2-chlorothioxanthone, and 2-isopropyl thioxanthone), benzyl 2-ethyl anthraquinone, methylbenzoyl formate, 2-hydroxy-2-methyl-1-phenyl propane-1-one, 2-hydroxy-4'-isopropyl-2-methyl propiophenone, e-hydroxy ketone, tetramethylthiuram monosulfide, allyl diazonium salt, and a combination of camphorquinone or 4-(N,N-dimethylamino) benzoate.

Any of a variety of different crosslinking mechanisms may be employed, such as thermal initiation (e.g., condensation reactions, addition reactions, etc.), electromagnetic radiation, and so forth. Some suitable examples of electromagnetic radiation that may be used include, but are not limited to, electron beam radiation, natural and artificial radio isotopes (e.g., α, β, and γ rays), x-rays, neutron beams, positively-charged beams, laser beams, ultraviolet, etc. The wavelength λ of the radiation may vary for different types of radiation of the electromagnetic radiation spectrum, such as from about $10^{-14}$ meters to about $10^{-5}$ meters. Besides selecting the particular wavelength λ of the electromagnetic radiation, other parameters may also be selected to control the degree of crosslinking. For example, the dosage may range from about 0.1 megarads (Mrads) to about 10 Mrads, and in some embodiments, from about 1 Mrads to about 5 Mrads.

In one embodiment, the polymer 12 can be acrylate-functionalized 18 at one chain-end as shown in FIG. 1. For instance, a PEG polymer that has been previously functionalized with short lactide/glycolide segments at the termini can be reacted with acryloyl chloride in 1:1 molar ratio to produce a functionalized polymer that includes an acrylate at one chain-end.

In addition to short hydrophobic control segments 13, 15 and crosslinkable functionality 18, the polymer 12 can also be functionalized so as to enable conjugation with the desired signaling molecule 16. For instance, a polymer 12 can be end-functionalized with succinimide by reaction with N,N'-disuccinimidyl carbonate according to standard practice.

In general, the functionalized polymers will be cross-linked prior to conjugation with the desired signaling molecules. For instance, the functionalized polymers can be assembled in aqueous solution by dialysis and crosslinked (e.g., via UV radiation) to generate water-swollen nanogels 20. Following functionalization and crosslinking, the nanogels 20 can generally have a largest dimension of from about 10 nanometers to about 100 nanometers.

The signaling molecule 16 of choice can be conjugated to the crosslinked nanogels by reaction between the nanogel functionality 18 (e.g., a succinimide group) and a functionality of the signaling molecule (e.g., an amine group). By conjugation in the nanogels 20, the signaling molecule 16 can be prevented from diffusion into the organic phase of the encapsulating microcapsules and can be sequestered from release until the degradation of the surrounding microcapsule, upon which the nanogels can release the conjugated signaling molecule 16 according to the engineered sustained release profile.

A nanogel 20 may include as a signaling molecule 16 any biologically active compound (or combination thereof) as may affect a developing system. For instance, a nanogel 20 can include a signaling molecule 16 that can act as a signal for modifying cell adhesion, growth, or migration; for instance, in stimulating or promoting the adhesion, growth, or migration of the desirable cells, and/or inhibiting or stimulating the adhesion, growth, or migration of undesirable cells. Such compounds can include growth factors, hormones, extracellular matrix proteins and other cellular adhesion peptides identified in the extracellular matrix protein. Suitable signaling molecules may include, for example, TGFβ1, BMP7, IGF1, IHH, BMP2, epithelial growth factor (EGF), acidic or basic fibroblast growth factor (FGF), vascular endothelial growth factor (VEGF), hepatocyte growth factor (HGF), heparin binding growth factor (HGBF), transforming growth factor (TGF), nerve growth factor (NGF), muscle morphogenic factor (MMP), and platelet derived growth factor (PDGF). Examples of extracellular matrix proteins include fibronectin, collagens, laminins, and vitronectins, and the tri-peptide RGD (arginine-glycine-aspartate) that is found in many of the extracellular matrix proteins. A signaling molecule can also be included to induce the ingrowth of desirable cells, e.g., smooth muscle cells and epithelial cells. Signaling molecules that inhibit or stimulate undesired cells, such as cancerous cells or inflammatory cells, can be included.

A signaling molecule may also include a small molecule such as a bisphosphonate that can prevent the loss of bone mass. Another example of a small molecule signaling molecule is an antibiotic that can prevent bacterial contamination. Examples of small molecule bisphosphonates include, without limitation, Etidronate, Clodronate, Tiludronate, Pamidronate, Neridronate, Olpadronate, Alendronate, Ibandronate, Risedronate, Zoledronate, and the like, as well as mixtures of bisphosphonates. Example of antibacterial agents include, without limitation, gentamicin, tetracycline, vancomycin, ibuprofen, dexamethasone, ciprofloxacin, gatifloxacin, polymyxin B and the like, as well as mixtures of the antibacterial small molecules. Of course, different types of signaling molecules (e.g., proteinaceous and small molecule, bisphosphonates, and antibacterial agents, etc.) can be combined in individual nanogels or in different nanogels held in the same or different microcapsules of a composition.

In general, the nanogels 20 can include the signaling molecules 16 in a concentration of from about 0.5 µg/mL to about 4 µg/mL per 20 mg of nanogels.

In forming a composition, a plurality of signaling molecule-conjugated nanogels 20 can be encapsulated in a polymer microcapsule 10 that can provide for delayed release of the nanogels 20 and the signaling molecules 16 carried by the nanogels 20. For instance, and as schematically illustrated in FIG. 1, a plurality of nanogels 20 can be encapsulated in a polylactide-based polymer microcapsule 10 according to a water-oil-water (w-o-w) double emulsion technique for delayed release of the signaling molecules. The polymer utilized in formation of the microcapsule 10 can be selected to provide a desired degradation rate and delay for the microcapsules. For instance, a poly(lactide-co-glycolide) (PLGA)-based microcapsule can be selected in design of materials for relatively rapid release of the contained nanogels (e.g., delays of up to about 6 weeks), while more hydrophobic polymers, such as a poly(lactide-co-caprolactone) (PLCL) copolymer, may be preferred to achieve longer delay times and release rates from the microcapsules. Polylactide homopolymers, as well as other lactide-based copolymers as are known in the art, may alternatively be utilized in formation of the microcapsules. In general, any hydrophobic polymer that can form microcapsules in aqueous solution can be used. Examples include, without limitation polyanhydrides, polyorthoesters, polyphosphazenes, polypropylene fumarate, polyhydroxy acids, polyhydroxybutyrate, polyvalerolactone, polymalonic acid, as well as mixtures of polymers.

A double emulsion w-o-w encapsulation technique, as may be utilized in forming the microcapsules 10 and as schematically illustrated in FIG. 1, can generally include dispersing the nanogels 20 in a first aqueous phase 30. Following, the aqueous phase 30 can be dispersed in a suitable organic phase 32 comprising an organic solution of the polymer (e.g., a poly(D,L lactide-co-glycolide) polymer) 34, the organic phase 32 being non-miscible with the aqueous phase 30. For example, a nanogel dispersion including about 0.1 mg nanogels/mL or greater, or from about 1 mg/mL to about 100 mg/mL, or even greater in some embodiments, can be injected (such as with a 25 gauge needle) into the organic polymer phase 32 while homogenizing, e.g., at about 15,000 to 25,000 rpm.

By way of example, an aqueous phase 30 including the nanogels 20 can be initially emulsified in an organic phase 32 including PLGA polymer of a predetermined molecular weight, poly(lactide-co-ethylene oxide fumarate) (PLEOF) as an emulsifying agent, and chloroform as an organic solvent. Other organic solvents and emulsifying agents as are known in the art may alternatively be utilized. For instance, organic solvents can include, without limitation, methylene chloride, ethyl acetate with or without benzyl alcohol or acetone, and combinations of organic solvents.

After this first homogenization (generally about 0.5 to about 5 minutes; for instance, for about 1 minute), this emulsion 35 is added to a second aqueous emulsification solution 36 to form a second emulsion. The second emulsification aqueous solution 36 can be for instance, a polyvinyl alcohol solution, optionally including ethyl acetate. The w-o-w emulsion mixture is mixed at high speed (generally about 1700 to 2500 rpm) to generate the microcapsules 10 including the polymer 34 surrounding the nanogels 20.

The stable microcapsules 10, each encapsulating a plurality of nanogels 20, can be formed and collected upon evaporation of the organic solvent (e.g., at ambient conditions, dependent upon the solvent) and centrifugation to remove the aqueous phase, as shown.

When considering formation of an injectable composition, the microcapsules can generally be formed with a largest external dimension of from about 1 μm to about 10 μm. However, the microcapsules are not limited to this size and larger materials may be preferred in certain applications. For example, when considering in vitro applications, it may be preferred to form larger microcapsules.

Design factors that may be modified to provide microcapsules with a desired size and degradation delay can include molecular weight, the type of polymer 34, emulsifier concentration in the organic phase, copolymer component ratio on a polymer (e.g., L:G ratio for a PLGA copolymer), and polymer concentration in the organic phase (affects capsule wall thickness). In general, lactide-based polymers (PLGA, PLCL, PLA, etc.) for use in the disclosed microcapsules can have a number average molecular weight of from about 5 kDa to about 75 kDa and a lactide copolymer ratio (e.g., L:G ratio) of from about 100:0 to about 50:50. The organic phase can generally include the emulsifying agent (e.g., the PLOEF) at a concentration of from about 5 wt. % to about 50 wt. %, and can include the lactide-based polymer at a concentration of from about 5 wt. % to about 15 wt. % in the organic solvent.

The composite nanogel/microcapsules can have a conjugation efficiency of the signaling molecules of greater than about 90% and a release level of greater than about 75%.

Figure 2:
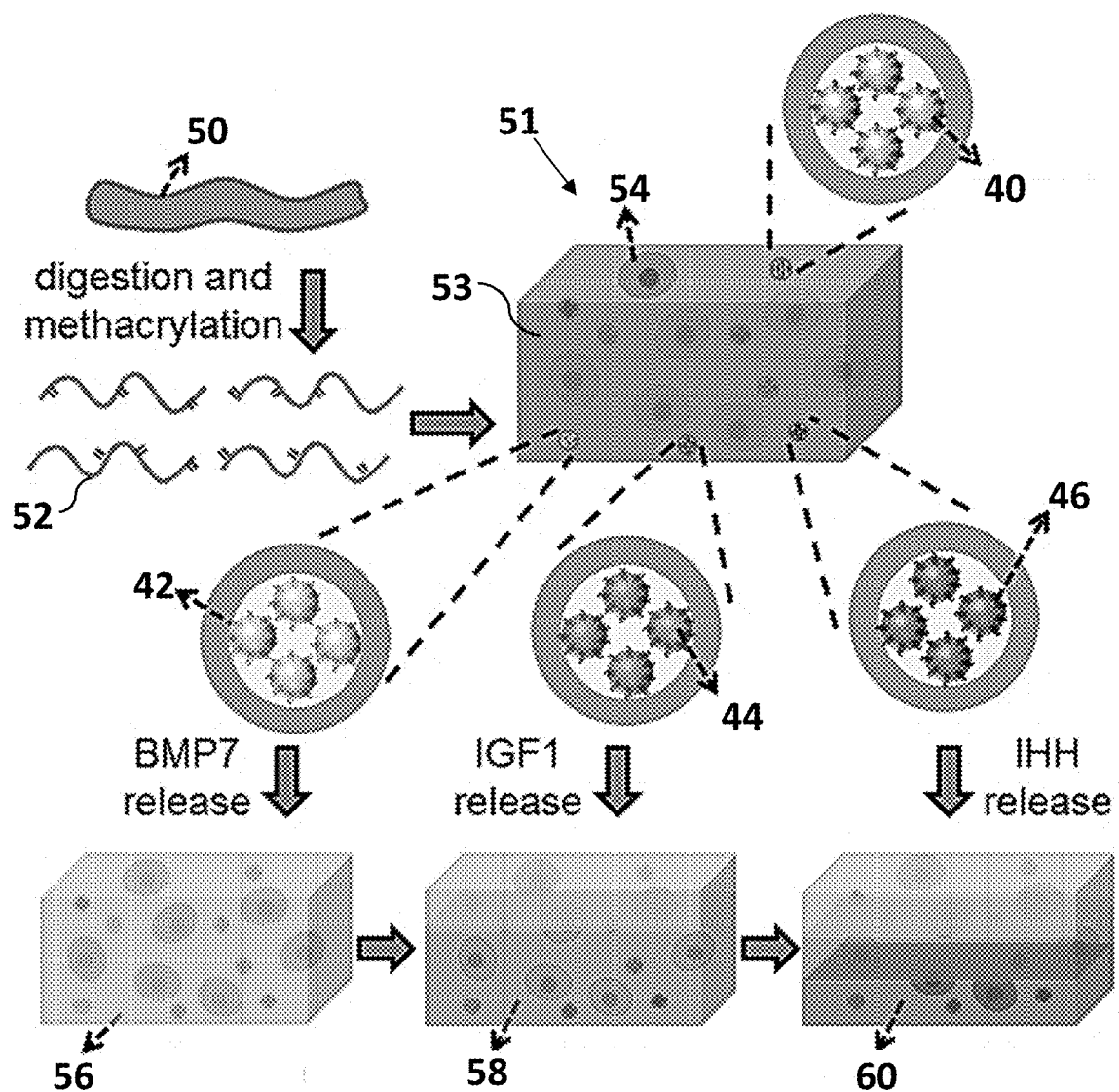
FIG. 2 schematically presents an approach to in situ formation of zonal regeneration of articular cartilage as may be carried out by use of disclosed compositions.

A composition can incorporate a plurality of different microcapsules so as to provide for sequential release of the signaling agents carried by the microcapsules. For instance, when considering a composition designed to encourage formation of articular cartilage, a composition can incorporate microcapsules designed for sequential, sustained release of TGFβ1, BMP7, IGF1, and IHH morphogens to generate the zonal structure of articular cartilage. For example, and as schematically illustrated in FIG. 2, a first type of microcapsule 40 of the composition can incorporate TGFβ1-conjugated nanogels and can be designed for release of the TGFβ1 over the entire course of the protocol (e.g., over weeks 1-9 of a 9-week protocol). A second type of microcapsule 42 of the composition can incorporate BMP7-conjugated nanogels and can be designed to release the BMP7 over weeks 1-3 of the protocol. A third type of microcapsule 44 of the composition can incorporate IGF1-conjugated nanogels and can be designed to release the IGF1 over weeks 4-6 of the protocol. A fourth type of microcapsule 46 of the composition can incorporate IHH-conjugated nanogels and can be designed to release the IHH over weeks 7-9 of the protocol. A composition 51, as illustrated in FIG. 2, can thus provide for the sequential, sustained release of BMP7, IGF1, and IHH morphogens in situ.

Optionally, microcapsules can incorporate multiple different nanogels therein. For instance, in the above example, as TGFβ1 is released in conjunction with the other signaling agents, microcapsules of a composition can incorporate both TGFβ1-conjugated nanogels and nanogels carrying another signaling agent (BMP7-, IGF1-, or IHH-conjugated nanogels). Alternatively, nanogels can be formed to include multiple different types of signaling agents, e.g., both TGFβ1 and one of the other signaling agents together in a single nanogel.

A composition 51 can include the microcapsules and a crosslinkable matrix-forming polymer 52. The composition 51 can have suitable rheological characteristics for delivery (e.g., injectability). The matrix-forming polymer 52 can be crosslinked following placement (e.g., injection) of the composition to form a crosslinked matrix 53. In one embodiment, the crosslinkable polymer 52 can be based upon a natural biopolymer that can provide biocompatibility to the composition. In addition, the composition 51 can incorporate one or more additional components conducive to the desired tissue formation, e.g., ECM components. For example, and as illustrated in FIG. 2, a composition 51 can be derived from a natural tissue 50 (e.g., allograft or xenograft tissue) that can be decellularized, digested, and functionalized to provide the crosslinkable polymer 52 in conjunction with other components of the natural tissue 50 in an injectable, crosslinkable composition 51. As such, the composition 51 can provide both a crosslinkable polymer 52 capable of forming the hydrogel matrix 53 and other components conducive to the tissue engineering application.

By way of example, when considering formation of articular cartilage, the composition 51 can be based upon natural articular cartilage. As fetal articular cartilage is capable of spontaneous healing while avoiding fibrocartilage formation, in one embodiment, a crosslinkable polymer 52 can be derived from fetal articular cartilage, e.g., the injectable composition 51 can be based on digested, decellularized, and functionalized fetal bovine articular cartilage.

In one embodiment, fetal bovine cartilage can be decellularized by treatment with 10 mM TRIS/1% Triton®, 1 U/mL deoxyribonuclease, and 1 U/mL ribonuclease, as known. After freeze-drying, the decellularized material can be digested with pepsin until a clear suspension is obtained. The digested and decellularized material can then be functionalized to include a crosslinkable functionality (e.g., acrylate or methacrylate functionality) on the digested polymers. For instance, the material can be reacted with methacrylic anhydride to produce a methacrylated biopolymer-based, crosslinkable polymer 52. Maximum added reactivity content of the biopolymer (e.g., acrylate functionality) can be such that will not significantly affect biocompatibility of the composition 51.

In one embodiment, a composition 51 (including all additives) can have a viscosity of from about 5 mPa-s to about 15 mPa-s, so as to be injectable through a 0.43 mm microcatheter. A crosslinkable composition 51 can have a gelation time of about 1 minute or less and can have a compressive modulus following crosslinking of about 50 kPa to about 150 kPa, so as to support the developing tissue. However, viscosity, injectability, gelation time, and mechanical characteristics (e.g., compressive modulus) of the composition 51 and the crosslinked hydrogel 53 formed from the composition 51 are not limited to these values and can be varied; for instance, depending upon the specific application of the composition.

In one embodiment, the composition 51 can also include cells 54 that can be affected by the release of the signaling molecules. Depending upon the specific application of the composition, cells 54 contained in a composition 51 can include differentiated cells and/or stem cells. For instance, in one particular embodiment, a composition 51 can include mesenchymal stem cells (MSC).

Cells 54 can be loaded into a composition 51 at a density similar to that of the tissue type of interest. For instance, in one embodiment, a composition 51 can incorporate MSCs at a density of from about 50 million cells/mL to about 200 million cells/mL, which corresponds to that of adult and fetal articular cartilage, respectively.

The concentrations of the different microcapsules 41, 42, 44, 46 included in a composition 51 can vary so as to achieve the desired concentrations of the various signaling molecules. For instance, when considering the formation of articular cartilage, a composition can include microcapsules at a concentration to provide about 100 μg/mL BMP7, about 100 μg/mL IGF1, and about 2.5 μg/mL IHH. Further, it has been shown that TGFβ1 concentrations of 3 and 30 ng/mL can stimulate chondrogenic differentiation of MSCs to the superficial and calcified zone phenotypes, respectively. Thus, in this particular embodiment, a composition can include microcapsules that include TGFβ1-conjugated nanogels so as to provide TGFβ1 concentrations of 3, 15, and 30 ng/mL at various time points throughout a tissue generation protocol.

Following formation of the hydrogel precursor composition 51 that includes a crosslinkable polymer 52 and the signaling molecule-conjugated nanogel/microcapsule composites 40, 42, 44, 46, optionally in conjunction with living cells 54 and one or more ECM components (not illustrated in FIG. 2), the composition 51 can be placed in the desired tissue formation location (e.g., via injection) and crosslinked to form a crosslinked hydrogel 53. The in situ gelation time (e.g., the UV exposure time) can be varied (e.g., from about 1 minute to about 5 minutes) to reach a targeted compressive modulus for the crosslinked composition 53. For instance, following injection, the composition can be subjected to gelation for a time so as to reach the compressive modulus of the superficial zone of articular cartilage (about 80 kPa).

Figure 3:
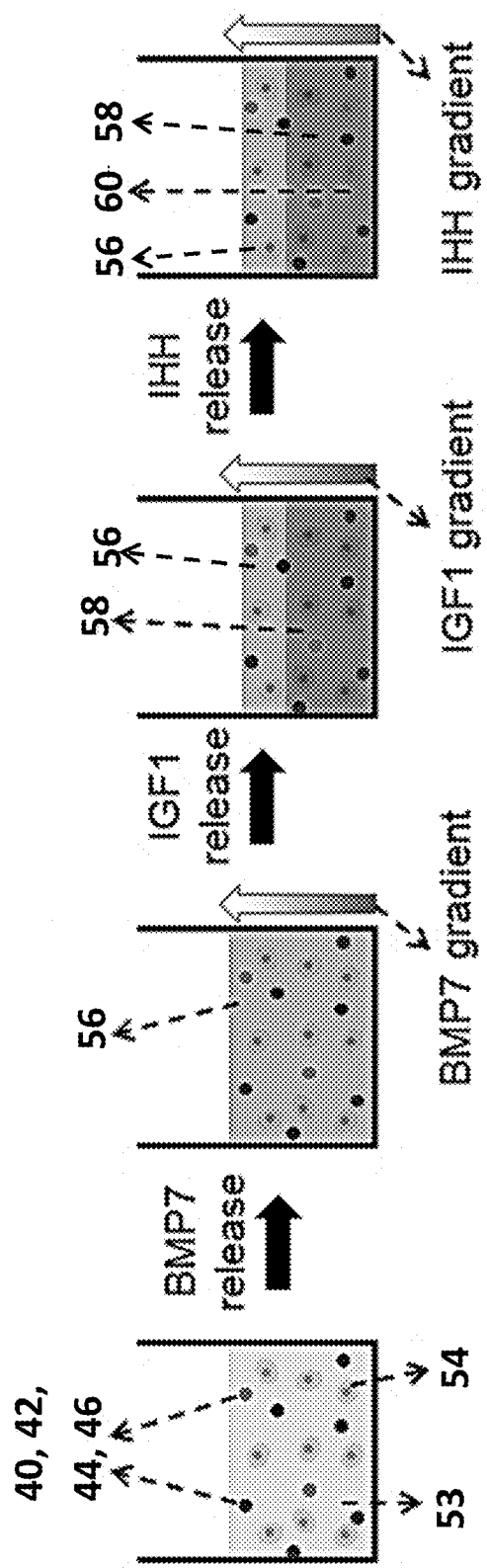
FIG. 3 is a schematic representation of gradient formation by sequential release of BMP7, IGF1, and IHH from different composite particles held in a hydrogel.

As illustrated in FIG. 2 and FIG. 3, following the placement and crosslinking of the hydrogel 53, the microcapsules 40, 42, 44, 46 can degrade according to the predetermined release profiles, which, in turn, can release the nanogels contained therein and allow for the sustained release of the signaling molecules contained in the nanogels. For example, following injection, crosslinking can be carried out to form a fetal articular cartilage-mimetic matrix 53 loaded with MSCs 54, TGFβ1-conjugated nanogel/microcapsules 40, BMP7-conjugated nanogel/microcapsules 42, IGF1-conjugated nanogel/microcapsules 44, and IHH-conjugated nanogel/microcapsules 46. The TGFβ1-conjugated nanogel/microcapsules 40 can begin to degrade relatively quickly following formation with the nanogels releasing the TGFβ1 over the entire course of the tissue formation (e.g., weeks 1-9), which can encourage condensation of the MSCs contained in the matrix. The BMP7-conjugated nanogel/microcapsules 42 can also begin to degrade relatively quickly following formation, and these nanogels can release the BMP7 over weeks 1-3 of the tissue formation. The release of the BMP7 in conjunction with the TGFβ1 can encourage chondrogenic differentiation of the MSCs to form a matrix similar to the superficial zone 56 of articular cartilage. The IGF1-conjugated nanogel/microcapsules 44 can begin to degrade following the predetermined delay period so as to release the IGF1 over weeks 4-6 of the tissue formation leading to the development of two distinct superficial 56 and middle zones 58 and the further differentiation of pre-chondrocytes to pre-hypertrophic chondrocytes. Release of IHH from the IHH-conjugated nanogel/microcapsules 46 following the predetermined delay period over weeks 7-9 of the tissue formation leading to the development of two distinct superficial 56 and middle zones 58 can lead to generation of the complete zonal organization of articular cartilage including the calcified zone 60.

Thus, the combination of delayed and sustained release of the signaling molecules in the composition can provide for in situ differentiation and maturation of cells that are either in the local area of the composition or contained in the composition itself so as to provide improved tissue generation and healing.

The present disclosure may be better understood with reference to the Examples set forth below.

EXAMPLE

Articular cartilage is structurally composed of multiple zones with distinct functions including the superficial zone for joint lubrication, middle zone for compressive strength, and calcified zone for load transfer to the underlying bone tissue. The superficial zone is characterized by pre-chondrocytes with high expression of superficial zone protein (SZP) for joint lubrication. The middle zone is characterized by pre-hypertrophic chondrocytes with high expression of glycosaminoglycans (GAG) and aggrecans (AGCs) for compressive strength. The calcified zone is characterized by hypertrophic chondrocytes with high expression of collagen type X (Col X) and alkaline phosphatase (ALP) for the formation of a mineralized matrix.

Figure 4:
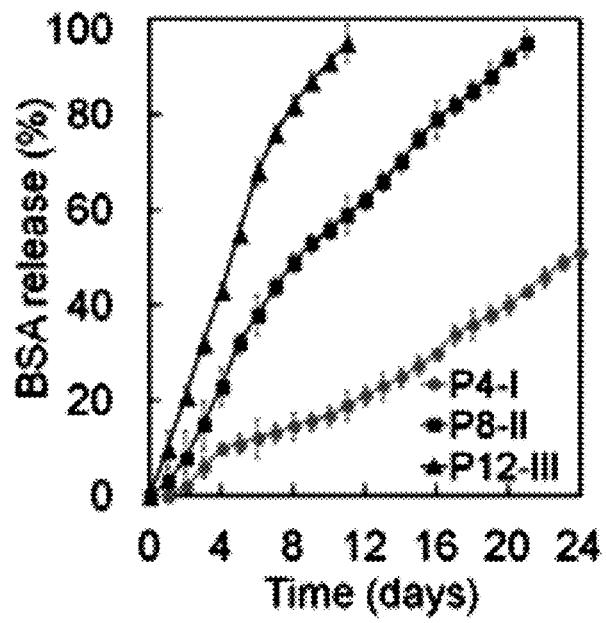
FIG. 4 graphically illustrates the effect of polymer molecular weight on the release rate for a protein conjugated to the polymer of a nanogel.
Figure 5:
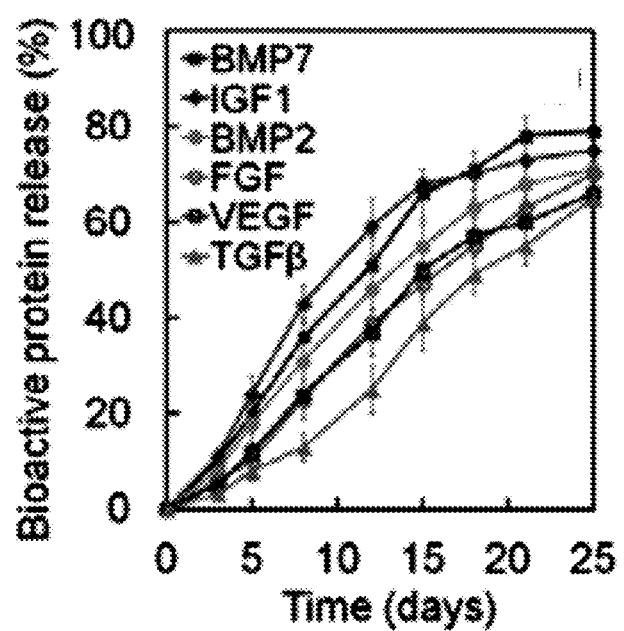
FIG. 5 presents the release kinetics of six different proteins from nanogels as described herein.
Figure 6:
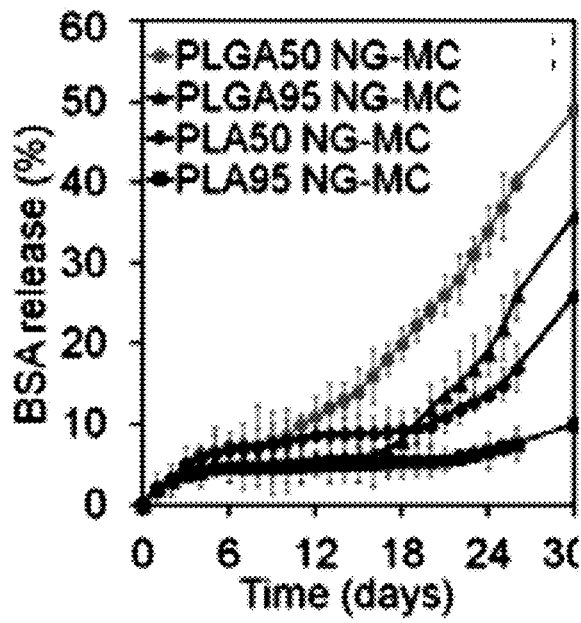
FIG. 6 illustrates the effect of modification in polymer/emulsifying agent concentration used in the formation of microcapsules on the delay time prior to release of protein from nanogels encapsulated within the microcapsules.

It has been demonstrated that proteins can be conjugated with high efficiency to nanogels based on polyethylene oxide macromers chain-extended with short lactide-glycolide segments (PEG-sLG) and the protein can be released with high bioactivity and at a prescribed rate. FIG. 4 shows that the release rate and duration of bovine serum albumin (BSA) conjugated to PEG-sLG nanogels can be controlled by changing the PEG molecular weight (P4-I—4 kDa PEG, P8-II—8 kDa PEG, P12-III—12 kDa PEG). FIG. 5 shows that different proteins (BMP7, BMP2, IGF1, TGFβ1, FGF, VEGF) conjugated to PEG-sLG nanogels are released at a prescribed rate with >60% bioactivity. FIG. 6 shows that BSA-conjugated nanogels formed of acrylated PEG-sLG (PEG-sLG-Ac) and further encapsulated in PLGA microcapsules (NG-MCs) release the protein after a predefined delay time ranging from a few days to 20 days, depending upon the polymer type and the PLEOF emulsifier concentration (PLGA50—PLGA copolymer using 50:50 wt. % PLGA:PLEOF in the organic phase; PLGA95—PLGA copolymer using 95:5 wt. % PLGA:PLEOF in the organic phase; PLA50—PLA homopolymer using 50:50 wt. % PLA:PLEOF in the organic phase; PLA95—PLA homopolymer using 95:5 wt. % PLA:PLEOF in the organic phase).

Figure 7:
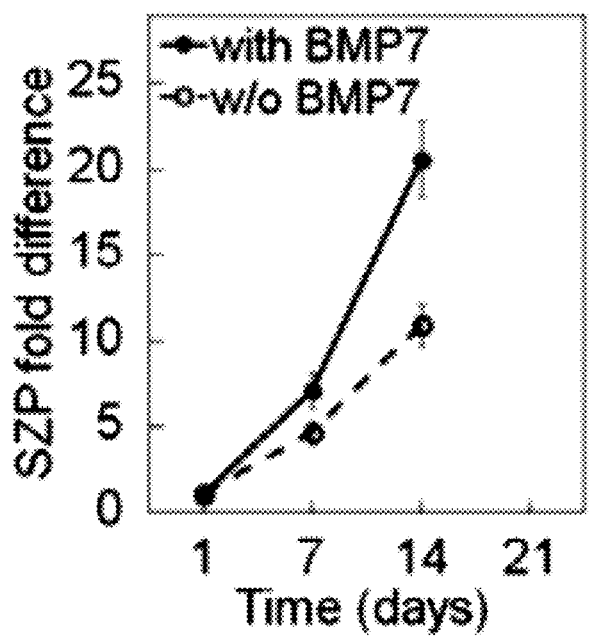
FIG. 7 illustrates the effect of TGFβ1/BMP7 release with incubation time on the expression of the cartilage superficial zone marker SZP from mesenchymal stem cells.
Figure 8:
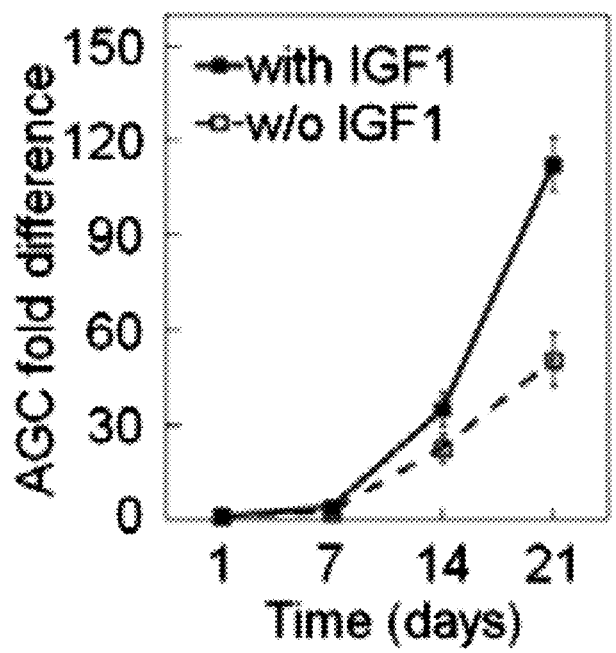
FIG. 8 illustrates the effect of TGFβ1/IGF1 release with incubation time on the expression of the cartilage middle zone marker AGC from mesenchymal stem cells.
Figure 9:
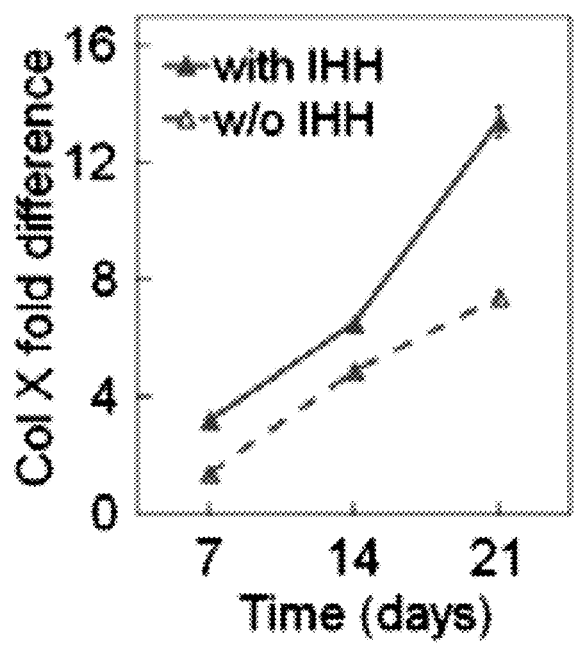
FIG. 9 illustrates the effect of TGFβ1/IHH release with incubation time on the presence of Col X in mesenchymal stem cells.

The combination of TGFβ1 and BMP7 stimulates chondrogenic differentiation of encapsulated mesenchymal stem cells to the superficial zone phenotype (FIG. 7); the combination of TGFβ1 and IGF1 stimulates the middle zone phenotype (FIG. 8); the combination of TGFβ1 and IHH stimulates the calcified zone phenotype (FIG. 9).

Figure 10:
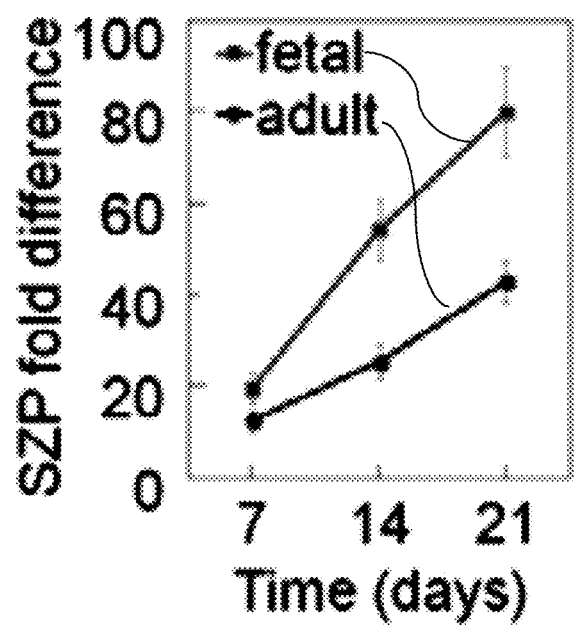
FIG. 10 compares a matrix based upon digested fetal articular cartilage with a matrix based upon digested adult articular cartilage with regard to the difference in the cartilage superficial zone marker SZP.
Figure 11:
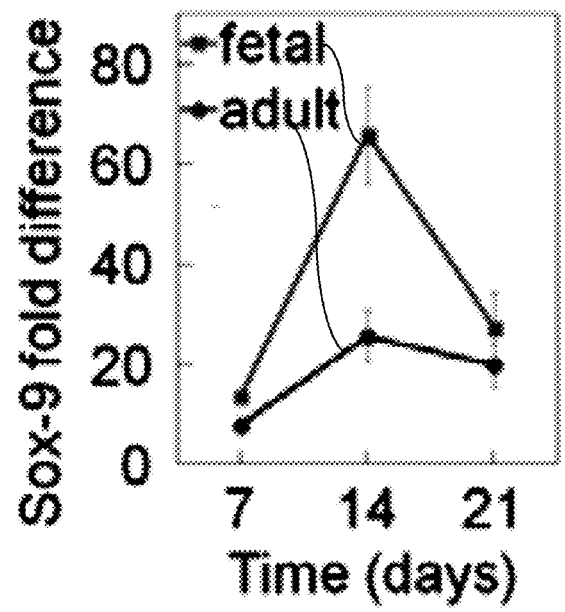
FIG. 11 compares a matrix based upon digested fetal articular cartilage with a matrix based upon digested adult articular cartilage with regard to the difference in the pre-chondrogenic marker Sox 9.
Figure 12:
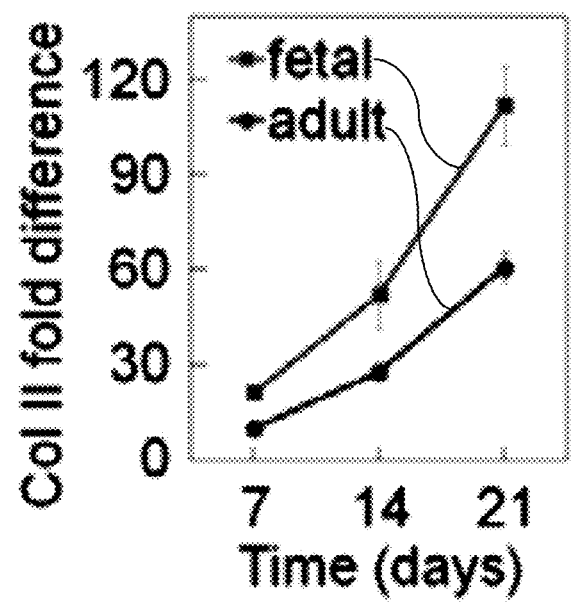
FIG. 12 compares a matrix based upon digested fetal articular cartilage with a matrix based upon digested adult articular cartilage with regard to the difference in the quantity of Col II.

Encapsulation of mesenchymal stem cells in a hydrogel based on digested bovine fetal articular cartilage and cultivation in chondrogenic medium supplemented with BMP7 sharply enhanced stem cell differentiation to the superficial zone phenotype compared to that of adult articular cartilage (FIG. 10, FIG. 11, FIG. 12). As shown, human MSCs encapsulated in digested fetal bovine articular cartilage and cultured in chondrogenic medium have higher expression of pre-chondrogenic markers Sox-9 (FIG. 11), superficial zone protein (SZP) (FIG. 10), and collagen type II (Col II; FIG. 12) compared to those of adult cartilage.

These results support in situ zonal regeneration of articular cartilage by sequential/sustained release of zone-specific morphogens in an injectable fetal articular cartilage-derived matrix.

While certain embodiments of the disclosed subject matter have been described using specific terms, such description is for illustrative purposes only, and it is to be understood that changes and variations may be made without departing from the spirit or scope of the subject matter.

What is claimed is:

1. A method for engineering a tissue, comprising:
   placing a composition in an area, the composition comprising
   a) a plurality of first nanogels, each first nanogel including a first crosslinked degradable polymer conjugated to a first signaling molecule, the first degradable polymer exhibiting a first degradation rate in the area, the first signaling molecule stimulating formation or repair of a biological tissue, the first degradation rate of the first degradable polymer providing a first degradation rate to the first nanogel;
   b) a plurality of first microcapsules, each first microcapsule carrying a plurality of the first nanogels, the first microcapsules each comprising a shell that includes a first bioerodible polymer;
   c) a plurality of second nanogels, each second nanogel including a second crosslinked degradable polymer conjugated to a second signaling molecule, the second degradable polymer exhibiting a second degradation rate in the area, the second signaling molecule stimulating formation or repair of the biological tissue, the second degradation rate of the second degradable polymer providing a second degradation rate to the second nanogel, the second degradation rate of the second nanogel differing from the first degradation rate of the first nanogel;
   d) a plurality of second microcapsules, each second microcapsule carrying a plurality of the second nanogels, the second microcapsules each comprising a shell that includes a second bioerodible polymer;
   e) a crosslinkable polymer; and
   crosslinking the crosslinkable polymer; wherein
   following the placing of the composition in the area, the first signaling molecule is released from the first microcapsules and the first nanogels according to a first release profile and the second signaling molecule is released from the second microcapsules and the second nanogels according to a second, different release profile.

2. The method of claim 1, wherein the composition is injected into the area.

3. The method of claim 1, wherein the first signaling molecule and the second signaling molecule are sequentially released from the composition.

4. The method of claim 1, the first degradable polymer having a first molecular weight and the second degradable polymer having a second molecular weight, the first and second degradation rates of the first and second degradable polymers being defined according to the first and second molecular weights.

5. The method of claim 1, the first degradable polymer comprising a first polyethylene glycol and the second degradable polymer comprising a second polyethylene glycol.

6. The method of claim 5, the first polyethylene glycol comprising a first hydrophobic segment at a terminus, and the second polyethylene glycol comprising a second hydrophobic segment at a terminus, wherein the second hydrophobic segment is more hydrophobic than the first hydrophobic segment.

7. The method of claim 1, the composition further comprising a plurality of living cells and/or one or more components of an extra-cellular matrix.

8. The method of claim 1, the first and second bioerodible polymers differing from one another according to one or more of number average molecular weight, presence or type of copolymer components, or ratio of a first copolymer component to a second copolymer component.

9. The method of claim 1, wherein the crosslinkable polymer comprises a biopolymer.

10. The method of claim 9, wherein the biopolymer is a cartilage derived biopolymer.

11. The method of claim 10, wherein the cartilage-derived biopolymer is an articular cartilage derived biopolymer.

12. The method of claim 1, the area comprising the biological tissue.

13. The method of claim 12, the biological tissue comprising a cartilage, bone, or another connective tissue.

14. The method of claim 13, the biological tissue comprising articular cartilage.

15. The method of claim 1, the composition further comprising additional microcapsules, the additional microcapsules carrying additional nanogels comprising additional crosslinked degradable polymers conjugated to additional signaling molecules.

16. The method of claim 1, wherein the first signaling molecule comprises TGFβ1, and the second signaling molecule comprises BMP7.

17. The method of claim 1, wherein the first signaling molecule is released according to a first sustained-release profile and the second signaling molecule is released according to a second sustained-release profile.

18. The method of claim 1, further comprising applying energy to the area, the energy crosslinking the crosslinkable polymer.

19. The method of claim 18, the energy comprising electromagnetic energy having a wavelength of from about $10^{-14}$ meters to about $10^{-5}$ meters and/or thermal energy.

20. The method of claim 1, wherein the crosslinkable polymer is crosslinked following the placing of the composition in the area.

* * * * *